United States Patent
Kumar et al.

(10) Patent No.: US 6,949,635 B1
(45) Date of Patent: Sep. 27, 2005

(54) DIDEOXY DYE TERMINATORS

(75) Inventors: Shiy Kumar, Solon, OH (US); Satyam Nampalli, Mayfield Heights, OH (US); Bernard F. McArdle, Twinsburg, OH (US); Carl W. Fuller, Cleveland Heights, OH (US)

(73) Assignee: Amersham Biosciences Corp, Piscataway, NJ (US)

( * ) Notice: Subject to any disclaimer, the term of this patent is extended or adjusted under 35 U.S.C. 154(b) by 0 days.

(21) Appl. No.: 09/699,030

(22) Filed: Oct. 26, 2000

Related U.S. Application Data

(63) Continuation of application No. 09/018,695, filed on Feb. 4, 1998, now abandoned.

(51) Int. Cl.$^7$ .......................... C07H 21/02; C12Q 1/68
(52) U.S. Cl. ....................... 536/23.1; 536/24.3; 435/6; 435/91.2
(58) Field of Search .................. 435/6, 91.2; 536/23.1, 536/24.3

(56) References Cited

U.S. PATENT DOCUMENTS

| | | | |
|---|---|---|---|
| 5,187,085 A | 2/1993 | Lee | 435/91 |
| 5,242,796 A | 9/1993 | Prober et al. | 435/6 |
| 5,306,618 A | 4/1994 | Prober et al. | 435/6 |
| 5,332,666 A | 7/1994 | Prober et al. | 435/91.5 |
| 5,558,991 A | 9/1996 | Trainor | 435/6 |
| 5,614,365 A | 3/1997 | Tabor et al. | 435/6 |
| 5,795,782 A | 8/1998 | Abramson et al. | |

FOREIGN PATENT DOCUMENTS

| | | | |
|---|---|---|---|
| WO | 91/05060 | 4/1991 | |
| WO | WO98/58942 | 12/1998 | C07H/19/04 |
| WO | WO 99/40223 | * 8/1999 | |

OTHER PUBLICATIONS

Evangelista et al, "Characterization of fluorescent nucleoside triphosphates by capillary electrophoresis with laser induced fluorescence detection: action of alkaline phosphatase and DNA polymerase", Anal. Biochem. 235:89–97.*

Haralambidis et al, "Preparation of base–modified nucleosides suitable for non–radioactive label attachment and their incorporation into synthetic oligodeoxyribonucleotides", Nucleic Acids Research 15(12):4857–4876.*

Fuller, C. W. et al., "Variation in band intensities in DNA sequencing," *Comments* 16(3):1–8 (1989).

Lee, L. G. et al., "DNA sequencing with dye–labeled terminators and T7 DNA polymerases: effect of dyes and dNTPs on incorporation of dye–terminators and probability analysis of termination fragments," *Nucl. Acids Res.* 20(10):2471–2483 (1992).

Parker, L. T. et al., "AmpliTaq® DNA polymerase, FS dye–terminator sequencing: analysis of peak height patterns," *BioTechniques* 21(4):694–699 (1996).

Parker, L. T. et al., "Peak height variations in automated sequencing of PCR products using Taq dye–terminator chemistry," *BioTechniques* 19(1):116–121 (1995).

Prober, J. M. et al., "A system for rapid DNA sequencing with fluorescent chain–terminating dideoxynucleotides," *Science* 238:336–341 (1987).

Rosenblum, B. B. et al., "New dye–labeled terminators for improved DNA sequencing patterns," *Nucl. Acids Res.* 25(22):4500–4504 (1997).

P.B. Vander Horn, "Thermo Sequenase™ DNA Polymerase and *T. acidophilum* Pyrophosphatase: New Thermostable Enzymes for DNA Sequencing", BioTechnics, vol. 22, No. 4 (1997) pp. 758–765.

* cited by examiner

*Primary Examiner*—Jeffrey Fredman
(74) *Attorney, Agent, or Firm*—Foley & Lardner LLP

(57) ABSTRACT

A kit for DNA sequencing comprising a first, second, third and fourth dye terminator molecules, each of the dye terminator molecules comprising a dye molecule, a linker of at least 10 atoms in length and either ddATP, ddCTP, ddGTP or ddTTP as a mono or tri-phosphate and a thermostable DNA polymerase.

8 Claims, 2 Drawing Sheets

DIDEOXY DYE TERMINATORS

RELATED APPLICATIONS

This application is a continuation of Kumar et al., U.S. application Ser. No. 09/018,695, filed Feb. 4, 1998, now abandoned.

FIELD OF THE INVENTION

This invention relates to dye terminator nucleic acid sequencing and reagents for such sequencing.

BACKGROUND OF THE INVENTION

The following is a discussion of the relevant art, none of which is admitted to be prior art to the appended claims.

Sequence reaction products must be labeled. This can be done using labeled primers, labeled nucleotides (usually radioactive dNTPs) or labeled ddNTP terminators. The use of labeled terminators has the advantage of leaving false-stops undetectable.

DNA sequence bands do not necessarily have uniform intensities. It is useful to express band intensity variability numerically. This can be done by reporting the ratio of maximum to minimum intensity of nearby bands (within a window of perhaps 40 bases)in a DNA sequence or, with normalization and correction for systematic "drift" in intensity by reporting the root mean square of band intensities (typically peak heights)(Fuller, C. W., *Comments* 16(3):1–8, 1989). It is advantageous to have uniformity of band intensity as sequence accuracy and read-length is improved with bands of more uniform intensity.

For accurate reading, the mobility of any given sequencing reaction product must migrate through the electrophoresis gel with a speed proportional only to its length. Products which migrate faster or slower than normal for a given length will result in sequence ambiguities or errors known as "compressions".

Anomalous migration speed can be caused by secondary structure of the DNA and is apparently the cause of most "compression" artifacts seen in radioactive-label (and other) sequencing experiments at GC-rich regions. These can often be resolved by the use of analogs of dGTP such as 7-deaza-dGTP or dITP. Another compression-like artifact is observed when some dye-labeled ddNTPs are used for sequencing. Several examples of this can be seen in Lee, L. G., Connell, C. R., Woo, S. L., Cheng, R. D., McArdle, B. F., Fuller, C. W., Halloran, N. C., and Wilson. R. K., *Nucleic Acids Res.,* 20:2471–2483, 1992 (see FIGS. 4g, 4h and 6h using ddCTP labeled with tetramethylbodipy and TMR or ddGTP labeled with bifluor). These compression-like artifacts are produced, even in sequences which are compression-free when sequenced radioactively or with dye-labeled primers. These artifacts can sometimes be eliminated by substituting dITP for dGTP or alpha-thio dNTPs for normal dNTPs (Lee, L. G. et al., *Nucleic Acids Res.,* 20: 2471–2483, 1992; U.S. Pat. No. 5,187,085). Similar artifacts seen with the fluorescein dye-labeled ddNTPs sold by Applied Biosystems for dye-terminator sequencing with T7 DNA polymerase are resolved by substituting alpha-thio dNTPs for normal dNTPs (Lee, L. G. et al., *Nucleic Acids Res.,* 20: 2471–2483, 1992; U.S. Pat. No. 5,187,085).

Prober, J. M., Trainor, G. L., Dam, R. J., Hobbs, F. W., Robertson, C. W., Zagursky, R. J., Cocuzza, A. J., Jensen, M. A. and Baumeister, K., *Science* 238:336–41 (1987) performed sequencing using terminators labeled with substituted succinyl-fluoresceins with linkers of 10 atoms in length, together with dATP, dCTP, dTTP, 7-deaza-dGTP and AMV reverse transcriptase, and a fluorescence-detecting instrument. From FIG. 6 of this paper is clear that overall band intensities varied by more than 10-fold, far more than the best available current methods with dye primers or radioactive labels.

Dideoxy NTP terminators that have the same basic structure as the Prober et al. (1987) terminators, but have four rhodamine dyes used in place of the succinyl fluoresceins and linkers of 5 atoms in length, have been used for sequencing with Taq polymerase. In order to use these terminators, dITP is used in place of dGTP or 7-deaza-dGTP to eliminate severe "compression" artifacts. This method has been practiced using cloned Taq DNA polymerase(Bergot, WO 9105060; Parker, L. T., Deng, Q, Zakeri, H., Carlson, C. Nickerson, D. A., Kwok, P. Y., *Biotechniques* 19(1) :116–121, 1995) and with a mutant of Taq polymerase (D49G, AmpliTaq CS) lacking 5'-3' exonuclease activity. However, band intensities vary by as much as 20-fold, limiting the accuracy and read-length possible with the method (Parker, L. T., Zakeri, H., Deng, Q., Spurgeon, S., Kwok, P. Y., Nickerson, D. A., *Biotechniques* 21(4): 694–699, 1996).

Lee, L. G., Connell, C. R., Woo, S. L., Cheng, R. D., McArdle, B. F., Fuller, C. W., Hallorand, N. D. and Wilson, R. K., *Nucleic Acids Res.,* 20:2471,1992)describe sequencing with a set of ddNTP terminators and T7 DNA polymerase. All have fluorescein-type dyes attached to the ddNTPs in essentially the same manner as the rhodamine terminators used for Taq sequencing. These are used with modified T7 DNA polymerase (Sequenase™ version 2.0) and alpha-thio dNTPs. The thio dNTPs are used to resolve the "compression" artifacts like dITP is used for the Taq dye-terminator methods. The results with this system are such that bands vary in intensity about 10-fold.

Wayne Barnes has published a protocol for dye-terminator sequencing with FY modified polymerases and $Mn^{2+}$ (Scientech Corp. St. Louis, Mo.). Bands are more uniform with this method varying about 4.5-fold at most.

Fluorescein-12 ddNTPs that have a linker length of 12 atoms and Biotin-11 ddNTPs that have a linker length of 11 atoms are available (Dupont NEN, Wilmington, Del.). These labeled ddNTPs are described as useful in sequencing reactions.

ABI PRISM disclose dichlororhodamine dyes linked to terminators by propargyl/ethylene oxide/amino ("EO") linkers eight atoms in length for sequencing (Rosenblum, B. B., Lee, L. G., Spurgeon, S. L., Khan, S. H., Menchen, S. M., Heiner, C. R., and Chen, S. M., *Nucleic Acids Res.* 25(22): 4500–4504, 1997).

Cyanine dyes have been utilized in dye terminators for sequencing (Lee et al., *Nucleic Acids Res.,* 20(10) :2471, 1992).

SUMMARY OF THE INVENTION

The present invention provides novel dideoxy dye-labeled terminators which are useful in a number of biological processes, including providing uniform band intensities and the resolution of dye-induced compression artifacts in DNA sequencing. The dideoxy dye-labeled terminators of the present invention are particularly well suited for use with DNA polymerases that are thermostable or which contain an altered dNMP binding site (Tabor et al., U.S. Pat. No. 5,614,365). Use of the terminators of the present invention for sequencing does not require the use of nucleotide analogs such as dITP or alpha-thio nucleotides to eliminate dye-induced compression artifacts. Applicant has surprisingly found that there is a strong correlation between the length of the link between the dye molecule and the nucleotide and band uniformity, but little correlation between the type of dye (or other parameters) and band uniformity. Dye terminators with linkers of 10 or more atoms (extended linkers) up to 25 atoms (10, 11, 12 . . . 25) when used in sequencing reactions produce bands in sequencing gels of significantly improved uniformity compared with dye terminators with linkers less than 10 atoms.

The dye termininators of the present invention with extended linkers typically are provided in groups of four (ATGC) with or without a thermostable DNA polymerase and are especially useful in a method of sequence analysis.

In a first aspect, the invention features a kit for DNA sequencing having a first, second, third and fourth dye terminator molecule, each of the dye terminator molecules has a dye molecule, a linker of at least 10 atoms in length and either ddATP, ddCTP, ddGTP or ddTTP as a mono or tri-phosphate and a thermostable DNA polymerase.

By "dye molecule" is meant any molecule that has a detectable emission spectrum, including but not limited to fluorescein, rhodamine, texas red, eosin, lissamine, coumarin, cyanine, and derivatives of these molecules. Dyes also include energy transfer dyes each comprising a donor and an acceptor dye.

By "linkers" is meant a chain of at least 10 atoms comprising carbon, nitrogen, and oxygen which links the dye molecule with thee dideoxynucleotide. The chain may also contain substituted carbon or sulfur. Linkage typically occurs at the aromatic base moiety of the nucleotide. The first two atoms of the linker attached to the base are typically joined in a triple bond.

By "substituted carbon " is meant that one or more hydrogens are replaced with a substitute group such as, but not limited to, hydroxyl, cyano, alkoxy, oxygen, sulfur, nitroxy, halogen, —N(CH$_3$)$_2$, amino, and —SH.

By "thermostable DNA polymerase" is meant a DNA polymerase has a half-life of greater than 5 minutes at 90° C. Such polymerases include, but are not limited to, DNA polymerases encoded by *Thermus aquaticus, Thermus thermophilus, Thermus flavus, Thermococcus littoralis, Pyrococcus furiosus, Thermotoga maritima,* and *Thermotoga neapolitana.*

In a preferred embodiment the thermostable DNA polymerase has an altered dNMP binding site so as to improve the incorporation of dideoxynucleotides relative to the natural polymerase. A DNA polymerase with an altered dNMP binding site does not discriminate significantly between dideoxynucleotides and deoxynucleotides. The chance of incorporating a dideoxynucleotide is approximately the same as that of a deoxynucleotide or at least 1/10 the efficiency of a deoxynucleotide.

In a second aspect the invention features a compound of formula (I)

A
|
B
|
C

A is a cyanine dye of the structure

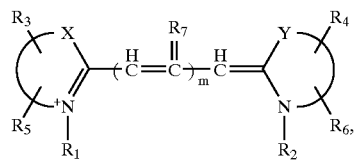

wherein the curved lines represent carbon atoms necessary for the formulation of cyanine dyes; X and Y are selected from the group consisting of O, S, and CH$_3$-C-CH$_3$; m is an integer selected from the group consisting of 1, 2, 3, and 4; R1, R2, R3, R4, R5, R6, and R7 are independently selected from the group consisting of H, OH, CO$_2$H, sulfonic acid or sulfonate groups, esters, amides, ethers, alkyl or aryl groups, and B and one R1, R2, R3, R4, R5, R6 or R7 is B.

B is a linker of at least 10 atoms in length wherein the atoms are selected from the group consisting of carbon, nitrogen, oxygen, substituted carbon and sulfur and the linker is attached at one end to A and at the other end to C.

C is a dideoxynucleotide selected from the group consisting of:

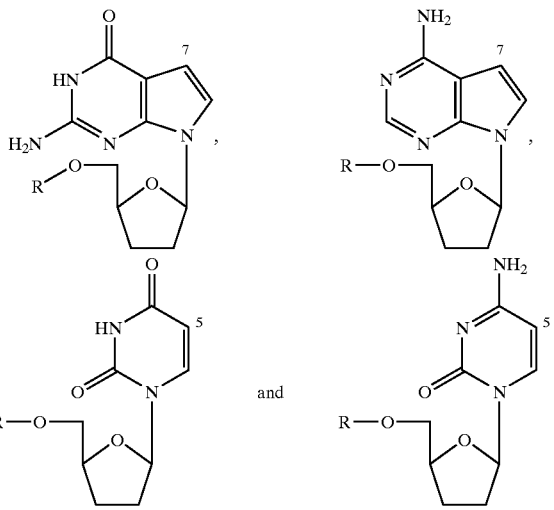

and wherein the linker is covalently bonded to the dideoxynucleotide at position 7 for the purines (ddG, ddA) and at position 5 for the pyrimidines (ddT, ddC) and wherein r is a mono or tri-phosphate.

The term "sulfonic acid or sulfonate groups" refer to SO$_3$H groups or salts thereof.

The term "ester" refers to a chemical moiety with formula —(R)n—COOR', where R and R' are independently selected from the group consisting of saturated or unsaturated alkyl and five-membered or six-membered aryl or heteroaryl moieties and where n is 0 or 1.

The term "amide" refers to a chemical substituent of formula —NHCOR, where R is selected from the group consisting of hydrogen, alkyl, hydroxyl, and five-membered or six-membered aryl or heteroaryl ring moieties, where the ring is optionally substituted with one or more substituents independently selected from the group consisting of alkyl, halogen, trihalomethyl, carboxylate, nitro, or ester.

The term "ether" refers to a chemical moiety with formula R-O-R' where R and R' are independently selected from the group consisting of saturated or unsaturated alkyl and five-membered or six-membered aryl or heteroaryl moieties and where n is 0 or 1.

The term "alkyl" refers to a straight-chain or branched aliphatic hydrocarbon. The alkyl group is preferably 1 to 10 carbons, more preferably a lower alkyl of from 1 to 7 carbons, and most preferably 1 to 4 carbons. Typical alkyl groups include methyl, ethyl, propyl, isopropyl, butyl, isobutyl, tertiary butyl, pentyl, hexyl and the like. The alkyl group may be substituted and some typical alkyl substituents include hydroxyl, cyano, alkoxy, oxygen, sulfur, nitroxy, halogen, —N(CH$_3$)$_2$, amino, and —SH.

The term "aryl" refers to an aromatic group which has at least one ring having a conjugated pi electron system and includes both carbocyclic aryl (e.g. phenyl) and heterocyclic aryl groups (e.g. pyridine). The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroarly" refers to an aryl group which contains at least one heterocyclic ring.

In a preferred embodiment the linker is selected from the group consisting of:
—C≡C—CH$_2$—NH—CO—(CH$_2$)$_5$—NH—CO—,
—C≡C—CH$_2$—NH—CO—(CH$_2$)$_5$—NH—SO$_2$—,
—C≡C—CH$_2$—NH—CO—(CH$_2$)$_{10}$—NH—CO—,
—C≡C—CH$_2$—NH—CO—(CH$_2$)$_5$—,
—C≡C—CH$_2$—NH—CO—(CH$_2$)$_5$—NH—CO—(CH$_2$)$_5$—, and
—C≡C—CH$_2$—NH—CO—(CH$_2$)$_5$—NH—CO—(CH$_2$)$_{10}$—NH—CO—

In preferred embodiments the dideoxy dye terminators are; a compound of the formula (II):

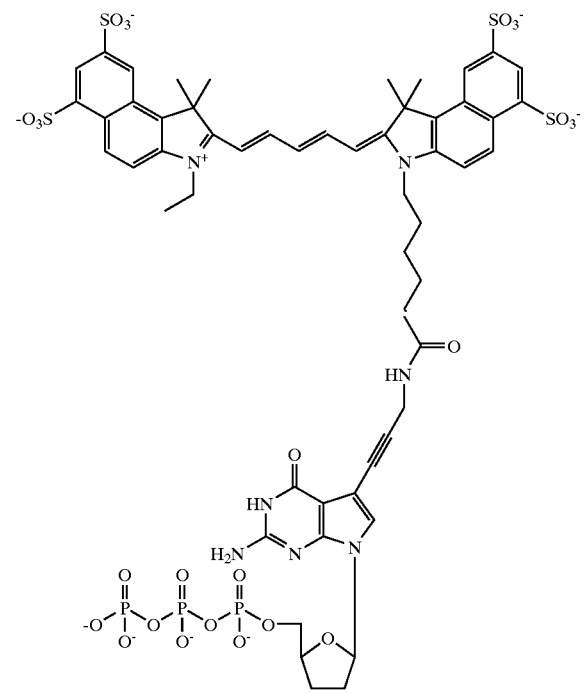

; a compound of the formula (III):

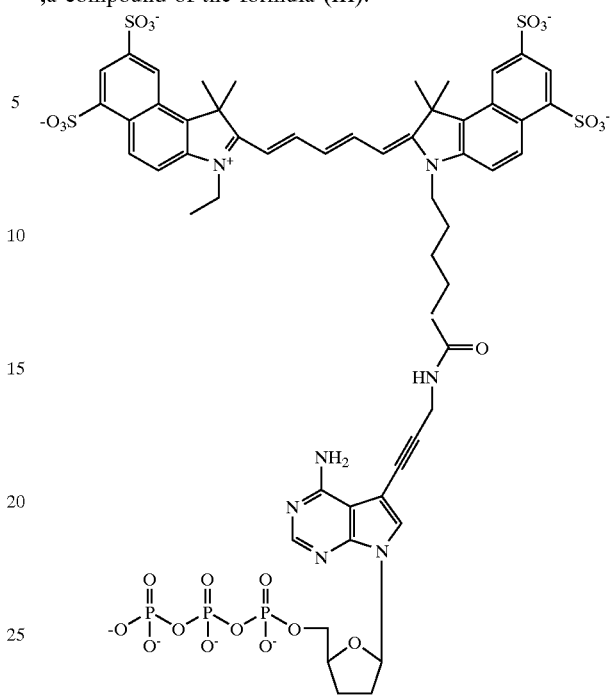

; a compound of the formula (IV):

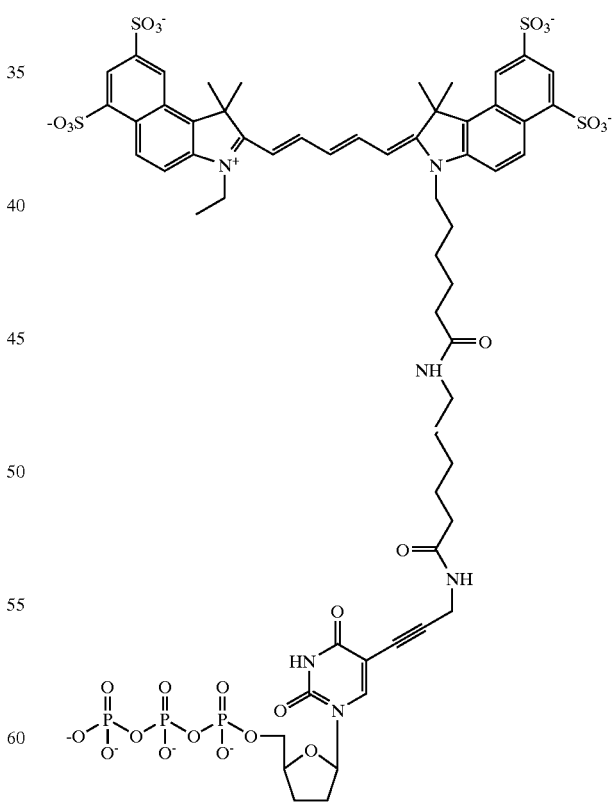

;compound of the formula (V):

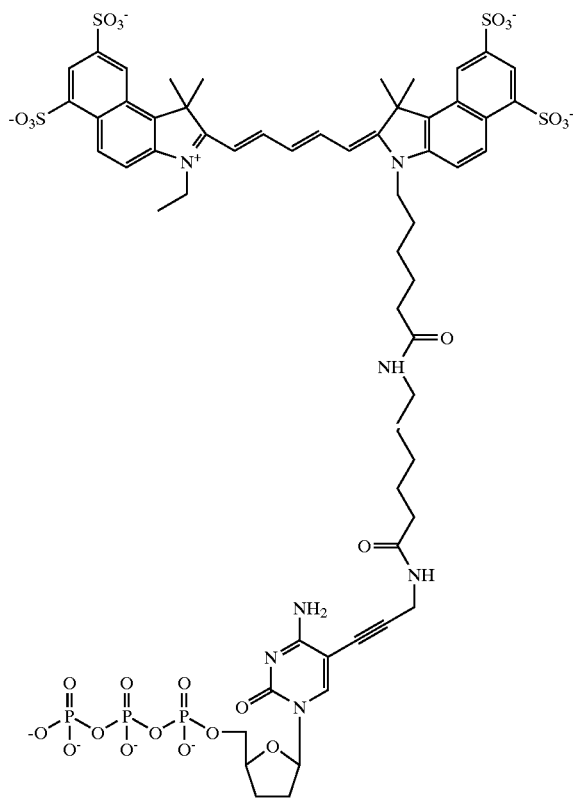

The Cy-5.5 ddGTP and ddCTP compounds have a linker of 10 atoms in length. The Cy-5.5 ddCTP and ddTTP compounds have a linker of 17 atoms in length.

In a third aspect the invention features a deoxyribonucleic acid sequence containing the compound of formula I, II, III, IV or V.

In a preferred embodiment the invention features a kit for DNA sequencing comprising compounds of formula II, III, IV, and V.

In a further preferred embodiments the kit further has a thermostable DNA polymerase; the thermostable DNA polymerase has an altered dNMP binding site so as to improve the incorporation of dideoxynucleotides relative to the natural polymerase.

Applicant has surprisingly found that the one parameter that most strongly correlates with band uniformity is the length of the linker between the dye and the ddNTP. Applicant has found that by extending the linker length between the dye and the nucleotide for any dye:ddNTP combination to at least 10 atoms, that band uniformity is substantially improved and there are no dye-induced compression artifacts.

Thus, in a fourth aspect, the invention features a method for determining the nucleotide base sequence of a DNA molecule consisting of the steps of incubating a DNA molecule annealed with a primer molecule able to hybridize to the DNA molecule in a vessel containing a thermostable DNA polymerase, a dye terminator with a linker of at least 10 atoms between the dye and the nucleotide and separating DNA products of the incubating reaction according to size whereby at least a part of the nucleotide base sequence of the DNA molecule can be determined.

In preferred embodiments, the dye terminator is a compound of formula I, II, III, IV or V; the thermostable DNA polymerase has an altered dNMP binding site.

Other features and advantages of the invention will be apparent from the following description of the preferred embodiments thereof, and from the claims.

All articles, publications and patents cited in this application are hereby incorporated by reference, in their entirety.

DESCRIPTION OF THE PREFERRED EMBODIMENTS

Figure 1:
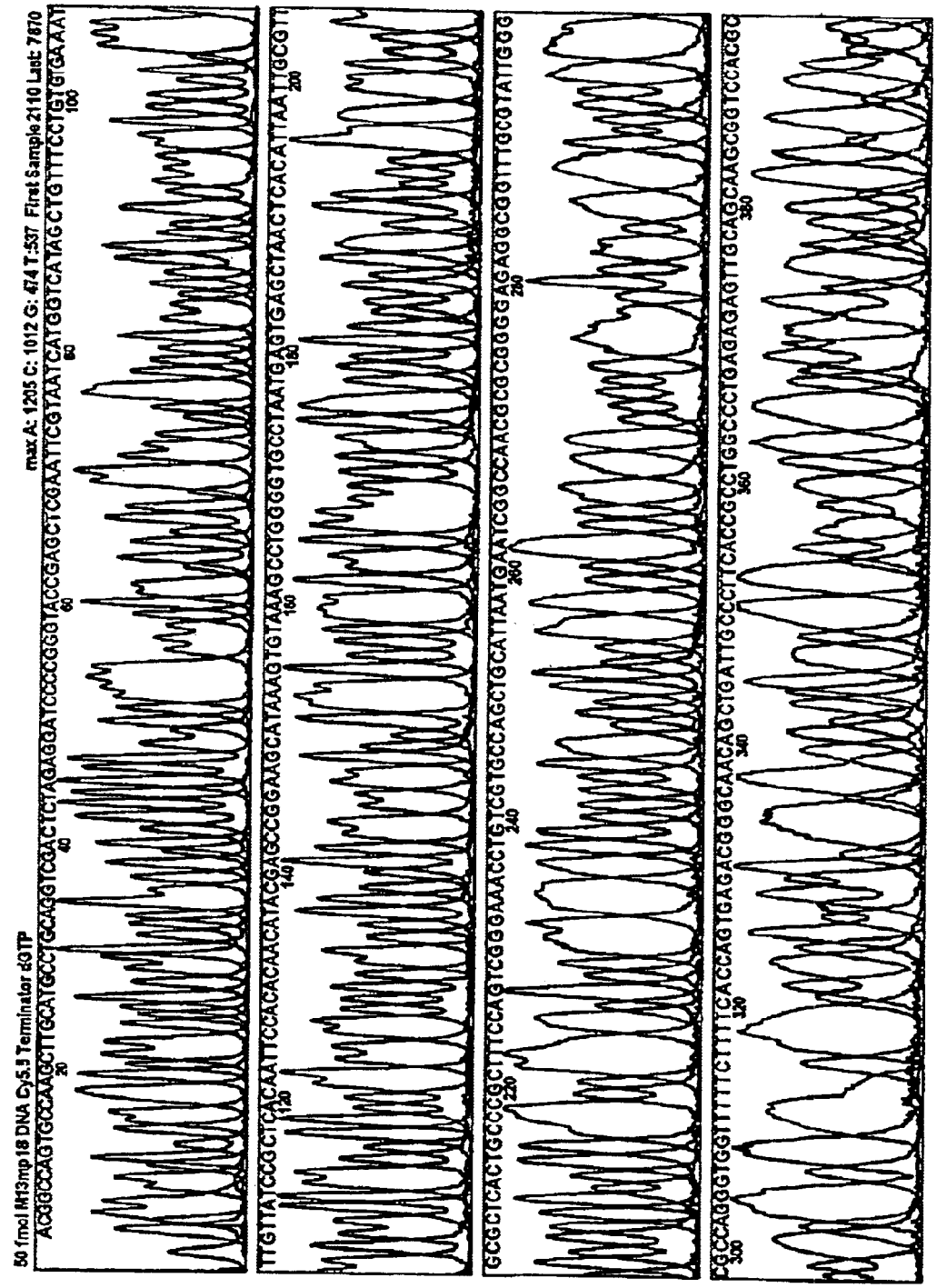
FIG. 1 presents DNA sequence data (SEQ ID NO:2) generated using M13mp18 containing a 115 bp SauAI fragment from lambda inserted a the BamHI site and Cy5.5 ddGTP, ddATP, ddTTP, and ddCTP dye terminators.

The following Examples are provided for further illustrating various aspects and embodiments of the present invention and are in no way intended to be limiting of the scope.

EXAMPLE 1

Synthesis of Dideoxy Dye Terminators Cy 5.5 Dideoxynucleoside Triphosphates

Dye terminators labeled with Cy5.5 were prepared from propargylaminodideoxynucleotids (Prober, J. M., Trainor, G. L., Dam, R. J., Hobbs, F. W., Robertson, C. W., Zagursky, R. J., Cocuzza, A. J., Jensen, M. A. and Baumeister, K., Science 238:336–41 (1987); U.S. Pat. Nos. 5,242,796, 5,306,618, and 5,332,666) and "CyDye Fluorolink Cy5.5 mono reactive dye" product PA25501 (Amersham Life Science) to produce compounds II, III, IV, and V. In the case of ddG and ddA, the propargylaminonucleotide was directly reacted with the N-hydroxysuccinimidyl ester of the Cy5.5 dye. In the case of ddC and ddT, a longer linker was constructed by reacting the propargylaminonucleotide with the N-hydroxysuccinimidyl ester of N-trifluoroacetyl-6-aminocaproic acid followed by hydrolysis in aqueous ammonia of the trifluoroacetyl group. The resulting compound was then reacted with the N-hydroxysuccinimidyl ester of the Cy5.5 dye to give the 17-atom linker between the Cy 5.5 dye and the pyrimidine base.

In addition to Cy 5.5 dyes, those who practice the art would know how to identify and utilize other dyes, including other cyanine dyes, with the appropriate optical properties. Also, the construction and attachment of various linkers is well known in the art. Suitable reagents for linker construction include one or more compounds consisting of activated forms of amino-protected alkyl or aryl amino acids such as compounds of the formula R—NH—(CH$_2$)$_n$—CO$_2$R' or R—NH—(CH$_2$)$_n$X(CH$_2$)$_m$—CO$_2$R', where R is an acid- or base-labile protecting group, R' is a reactive ester or anhydride group, X is aryl, O, S, or NH, and where n and m are 0–12. Other linkers constructed by N— or O— or S— alkylation are also suitable. The exact linker length, of at least 10 atoms, for a specific dye and dideoxynucleotide combination can be determined empirically by monitoring band uniformity in DNA sequencing as described (see Example 3).

EXAMPLE 2

Dye Terminator Cycle Sequencing

DNA cycle sequencing was carried out using Thermo Sequenase™ DNA polymerase (Amersham, Cleveland, Ohio) and Cy5.5 dideoxy dye terminators using the following cycle sequencing protocol:

1. A master mix was prepared consisting of the following:

| | |
|---|---|
| Template DNA | 5.0 μl |
| 10X Reaction buffer (see below) | 3.5 μl |
| Primer, 2 μM | 1.0 μl |
| Polymerase (see below) | 2 μ |
| H₂O | 15.5 μl |
| Total volume | 27.0 μl |

10× Reaction Buffer:
150 mM Tris HCL pH 9.5
35 mM MgCl₂
Polymerase: Thermo Sequenase™ DNA polymerase, 10 U/μl, 0.0017U/μl, *Thermoplasma acidophilum* inorganic pyrophosphatase: 20mM Tris-HCl, pH 8.5, 1 mM DTT, 0.1 mM EDTA, 0.5% Tween-20, 0.5% Nonidet P-40 and 50% glycerol.

2. Four microcentrifuge tubes were labeled and 2 μl of Cy5.5 labeled ddG, ddA, ddT, ddC solution was added to each tube.

25:1 ddG Mix, 300 μM each of dGTP, dATP, dTTP & dCTP, 12 μM Cy5.5 ddGTP
25:1 ddA Mix, 300 μM each of dGTP, dATP, dTTP & dCTP, 12 μM Cy5.5 ddATP
25:1 ddT Mix, 300 μM each of dGTP, dATP, dTTP & dCTP, 12 μM Cy5.5 ddTTP
25:1 ddC Mix, 300 μM each of dGTP, dATP, dTTP & dCTP, 12 μM Cy5.5 ddCTP 3. Six μl of the master mix (from step 1) was aliquoted to each of the 4 tubes from step 2 above. Cycling was carried out as follows: 95° C. (30 sec), 45–55° C. (30 sec) and 72° C. (60 sec) for 35 cycles then incubate at 72° C. 5–7 minutes.

4. One μl of 8M ammonium acetate was added to each tube. Then 27 μl (approximately 3 times the reaction volume) of chilled 100% ethanol was added. Then mixture was mixed and placed on ice for 20 minutes to precipitate the DNA.

5. The mixture was centrifuged in a microcentrifuge (~12,000 rpm) for 20–30 minutes at either room temperature or 4° C. The supernatant was removed and then 200 μl of 70% ethanol was added to wash the DNA pellet.

6. The mixture was again centrifuged for 5 minutes, the supernatant removed and the pellet dried (in a vacuum centrifuge) for 2–3 minutes.

7. Each pellet was resuspended in 6 μl of formamide loading dye (Amersham, Cleveland, Ohio), vortexed vigorously (10–20 sec) to ensure that all DNA was dissolved. The mixture was briefly centrifuged to collect the sample at the bottom of the tube.

8. Samples were heated to 70° C. for 2–3 minutes to denature the DNA, then placed on ice.

9. Then 1.5–2 μl of the volume was loaded onto a lane of the sequencing gel, and the gel run on the MICRO Gene Blaster instrument (VGI).

For this sequence, the template DNA was M13mp18 containing a 115 bp Sau3AI fragment from bacteriophage lambda inserted at the BamHI site (product number US 70171 Amersham). The primer is the −40 Forward 23-mer universal primer (5'-GTTTTCCCAGTCACGACGTTGTA-3')(SEQ. ID. NO. 1). Results are shown in FIG. 1.

EXAMPLE 3

Correlation of Linker Length and Band Intensity Variability

Figure 2:
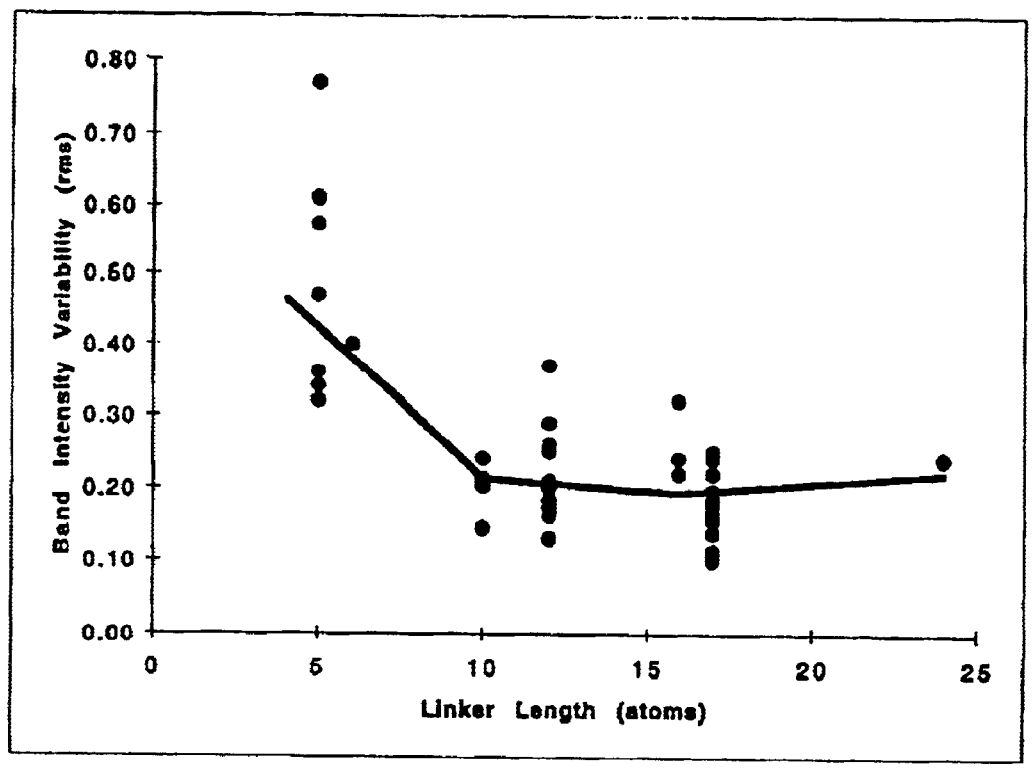
FIG. 2. is a graph of band intensity variability (rms) vs linker length (atoms).

Sequencing reactions were carried out as described in example 2 with various dye molecules linked to dideoxy-nucleotides with linkers of various lengths (see Table 1). The labeled DNA products were then separated on denaturing polyacrylamide gels and the labeled products were detected by fluorescence. The intensity of the bands is taken as the height of the peaks in a graph of fluorescence (in arbitrary units) against time. Typically, systematic variations in peak heights can be seen in graphs of peak heights plotted sequentially. These systematic variations in the peak heights can be modeled by least-square fitting to a second-order polynominal function. Dividing the peak height for each band by the value of the curve-fit polynomial function yields a normalized band intensity for each peak. Variation in these band intensities can be expressed as the square root of the variance $\sqrt{(n\Sigma x^2 - (\Sigma x)^2/n^2)}$ of the normalized peak heights, which can typically have values between 0 and 1 with more variability represented by higher numbers (Fuller, C. W., *Comnments* 16(3):1–8, 1989). This value is numerically equal to root-mean-square (RMS) value when 1.0 is subtracted from the normalized peak heights. These values are reported in Table 1 and graphed in FIG. 2. Variability of band intensities is significantly reduced when linkers of 10 or more atoms in length were used, resulting in sequence data that was easier to interpret accurately.

TABLE 1

| | Base | Dye[a] | Linker Length[b] | Band Uniformity (rms) |
|---|---|---|---|---|
| 1 | T | Coumarin | 5[c] | 0.32 |
| 2 | G | Lissamine | 5[d] | 0.77 |
| 3 | G | R110 | 5[e] | 0.34 |
| 4 | A | R6G | 5[e] | 0.32 |
| 5 | G | R6G | 5[e] | 0.57 |
| 6 | C | ROX | 5[e] | 0.36 |
| 7 | T | TMR | 5[e] | 0.47 |
| 8 | A | TxR | 5[d] | 0.61 |
| 9 | C | Eosin | 6[e] | 0.40 |
| 10 | G | Cy3 | 10[i] | 0.24 |
| 11 | A | Cy5 | 10[i] | 0.15 |
| 12 | G | Cy5 | 10[i] | 0.21 |
| 13 | A | Cy5.5 | 10[i] | 0.21 |
| 14 | G | Cy5.5 | 10[i] | 0.20 |
| 15 | A | Fl | 12[f] | 0.16 |
| 16 | C | Fl | 12[f] | 0.20 |
| 17 | G | Fl | 12[f] | 0.17 |
| 18 | T | Fl | 12[f] | 0.18 |
| 19 | A | R6G | 12[f] | 0.13 |
| 20 | T | R6G | 12[f] | 0.25 |
| 21 | A | ROX | 12[f] | 0.21 |
| 22 | T | ROX | 12[f] | 0.16 |
| 23 | C | TMR | 12[f] | 0.26 |
| 24 | G | TMR | 12[f] | 0.29 |
| 25 | T | TMR | 12[f] | 0.37 |
| 26 | A | TxR | 16[g] | 0.32 |
| 27 | C | TxR | 16[g] | 0.24 |
| 28 | G | TxR | 16[g] | 0.22 |
| 29 | U | TxR | 16[g] | 0.24 |
| 30 | A | Cy3–Cy5 | 17[j] | 0.11 |
| 31 | C | Cy3–Cy5 | 17[j] | 0.16 |
| 32 | G | Cy3–Cy5 | 17[j] | 0.22 |
| 33 | T | Cy3–Cy5 | 17[j] | 0.11 |
| 34 | C | Cy5 | 17[j] | 0.14 |
| 35 | T | Cy5 | 17[j] | 0.10 |
| 36 | C | Cy5.5 | 17[j] | 0.20 |
| 37 | T | Cy5.5 | 17[j] | 0.18 |
| 38 | A | Fl | 17[h] | 0.16 |

TABLE 1-continued

|  | Base | Dye[a] | Linker Length[b] | Band Uniformity (rms) |
|---|---|---|---|---|
| 39 | C | Fl | 17[h] | 0.24 |
| 40 | G | Fl | 17[h] | 0.18 |
| 41 | T | Fl | 17[h] | 0.25 |
| 42 | T | Fl | 24[k] | 0.24 |

[a]Abbreviations for dyes: Fl, Carboxyfluorescein; R110, Rhodamine 110; R6G, Rhodamine 6G; ROX, Rhodamine X; TMR, tetramethylrhodamine; TxR, Texas Red (Molecular Probes). The dyes Cy3, Cy3.5, Cy5 and Cy5.5 were from Amersham Life Science, Cleveland, OH.
[b]Linker length is the number of atoms between the ring structure of the nucleoside base (A, C, G or T) and the ring structure of the dye.
Linker structures
[c] —C≡C—CH$_2$—NH—CO—
[d] —C≡C—CH$_2$—NH—SO$_2$—
[e] —C≡C—CH$_2$—NH—CS—NH—
[f] —C≡C—CH$_2$—NH—CO—(CH$_2$)$_5$—NH—CO—
[g] —C≡C—CH$_2$—NH—CO—(CH$_2$)$_9$—NH—SO$_2$—
[h] —C≡C—CH$_2$—NH—CO—(CH$_2$)$_{10}$—NH—CO—
[i] —C≡C—CH$_2$—NH—CO—(CH$_2$)$_5$—
[j] —C≡C—CH$_2$—NH—CO—(CH$_2$)$_5$—NH—CO—(CH$_2$)$_5$—
[k] —C≡C—CH$_2$—NH—CO—(CH$_2$)$_5$—NH—CO—(CH$_2$)$_{10}$—NH—CO—

Other embodiments are within the following claims.

What is claimed is:

1. A compound of the formula (II):

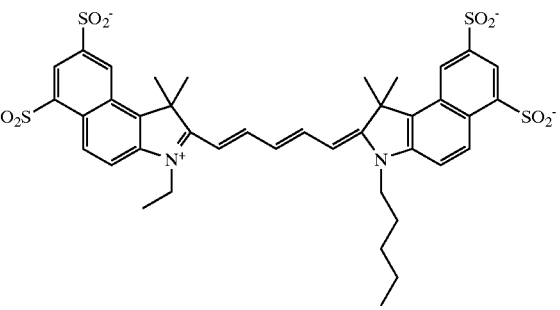

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 1
gttttcccag tcacgacgtt gta                                          23

<210> SEQ ID NO 2
<211> LENGTH: 391
<212> TYPE: DNA
<213> ORGANISM: Artificial Sequence
<220> FEATURE:
<223> OTHER INFORMATION: Description of Artificial Sequence: Cloning
      vector M13mp18

<400> SEQUENCE: 2
acggccagtg ccaagcttgc atgcctgcag gtcgactcta gaggatcccc gggtaccgag    60
ctcgaattcg taatcatggt catagctgtt tcctgtgtga aatttgttat ccgctcacaa   120
ttccacacaa catacgagcc ggaagcataa agtgtaaagc ctggggtgcc taatgagtga   180
gctaactcac attaattgcg ttgcgctcac tgcccgcttt ccagtcggga aacctgtcgt   240
gccagctgca ttaatgaatc ggccaacgcg cggggagagg cggtttgcgt attgggcgcc   300
agggtggttt tcttttcac cagtgagacg ggcaacagct gattgccctt caccgcctgg   360
ccctgagaga gttgcagcaa gcggtccacg c                                  391

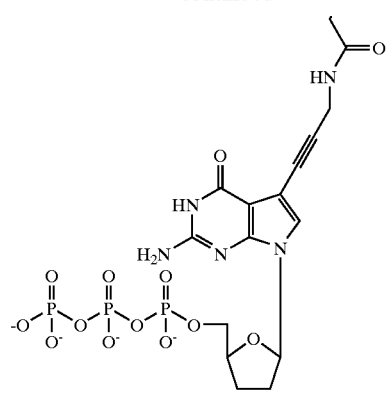

2. A compound of the formula (III):

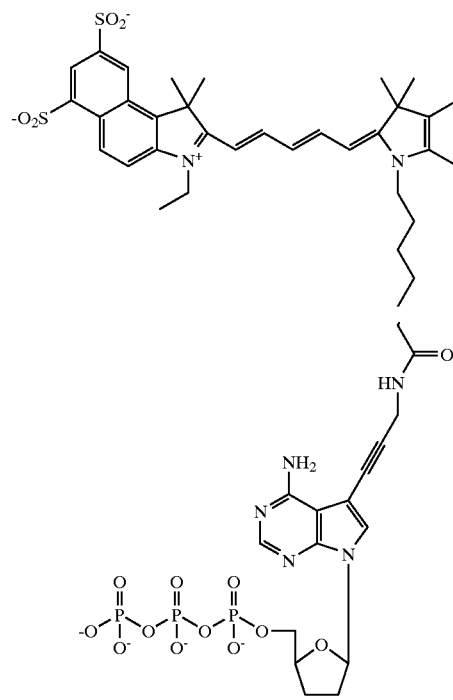

3. A compound of the formula (IV):

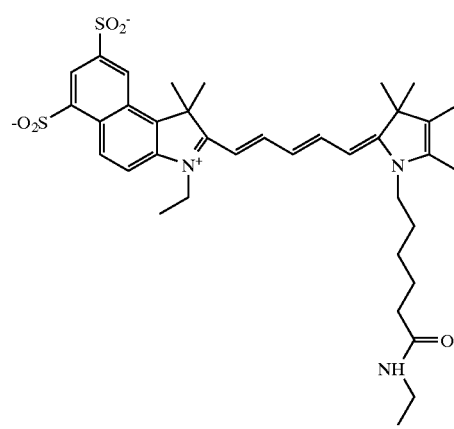

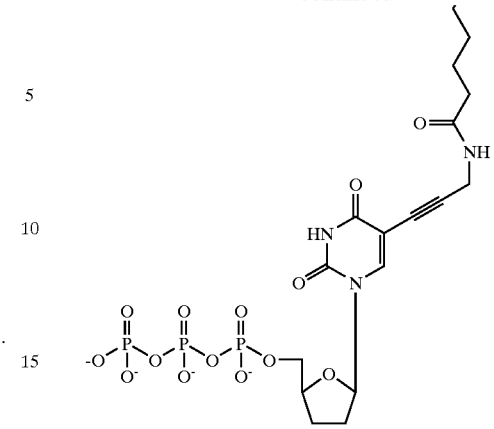

4. A compound of the formula (V):

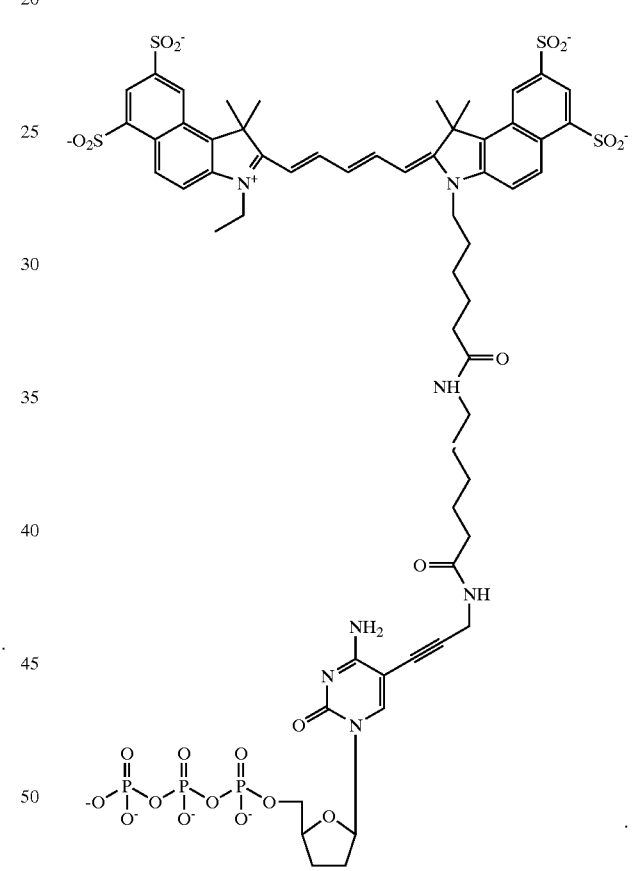

5. A deoxyribonucleotide sequence containing a compound of formula II, III, IV, or V.

6. A kit for DNA sequencing comprising compounds of formula II, III, IV, and V.

7. The kit of claim 6, further comprising a thermostable DNA polymerase.

8. The kit of claim 7, wherein said polymerase is a thermostable DNA polymerase that has an altered dNMP binding site so as to improve the incorporation of dideoxynucleotides relative to the natural polymerase.

* * * * *

UNITED STATES PATENT AND TRADEMARK OFFICE
CERTIFICATE OF CORRECTION

PATENT NO. : 6,949,635 B1
APPLICATION NO. : 09/699030
DATED : September 27, 2005
INVENTOR(S) : Shiv Kumar et al.

It is certified that error appears in the above-identified patent and that said Letters Patent is hereby corrected as shown below:

On The Title Page Item (75), "Shiy Kumar" should read --Shiv Kumar--.

Column 3, line 30, "linkers" should read --linker--.

Column 5, line 21, "heteroarly" should read --heteroaryl--.

Column 5, line 26, "-(CH$_2$)$_5$-" should read -- -(CH$_2$)$_9$- --.

Signed and Sealed this

Twelfth Day of June, 2007

JON W. DUDAS
*Director of the United States Patent and Trademark Office*